United States Patent [19]

Mücke

[11] Patent Number: 4,940,664

[45] Date of Patent: Jul. 10, 1990

[54] STABILIZATION OF CARRIER-BOUND ENZYMES BY TREATMENT WITH A BIFUNCTIONAL CROSSLINKING AGENT AND A POLYAMINE

[75] Inventor: Ingo Mücke, Barsinghausen, Fed. Rep. of Germany

[73] Assignee: Kali-Chemie Aktiengesellschaft, Hanover, Fed. Rep. of Germany

[21] Appl. No.: 197,436

[22] Filed: May 23, 1988

[30] Foreign Application Priority Data

Jun. 10, 1987 [DE] Fed. Rep. of Germany ....... 3719324

[51] Int. Cl.⁵ .................... C12N 11/14; C12N 11/00
[52] U.S. Cl. .................... 435/176; 435/174
[58] Field of Search ............. 435/174, 176, 177, 180, 435/181, 182

[56] References Cited

U.S. PATENT DOCUMENTS

| | | | |
|---|---|---|---|
| 3,796,634 | 3/1974 | Haynes et al. | 435/180 |
| 4,141,857 | 2/1979 | Levy et al. | 252/430 |
| 4,230,803 | 10/1980 | Weidenbach et al. | 435/176 |
| 4,251,631 | 2/1981 | Simon | 435/176 X |
| 4,337,172 | 6/1982 | Teague et al. | 252/430 |
| 4,438,196 | 3/1984 | Lantero, Jr. | 435/96 |
| 4,504,582 | 3/1985 | Swann | 435/108 |
| 4,519,538 | 7/1970 | Messing et al. | 195/63 |
| 4,533,633 | 8/1985 | Weidenbach et al. | 435/94 |
| 4,665,025 | 5/1987 | Weidenbach et al. | 435/94 |

FOREIGN PATENT DOCUMENTS 0133531 2/1987 European Pat. Off. .

*Primary Examiner*—David M. Naff
*Attorney, Agent, or Firm*—Foley & Lardner, Schwartz, Jeffery, Schwaab, Mack, Blumenthal & Evans

[57] ABSTRACT

The stability of granular carrier-bound enzymes is improved by further treating the carrier-bound enzyme with a bifunctional cross-linking agent and a polyamine. A particularly preferred cross-linking agent is glutaric dialdehyde, and a particularly preferred polyamine is polyethylene imine. Preferably, the cross-linking agent is used in an amount of 5 to 250 mg per 1 gram of carrier-bound enzyme and is dissolved in a 0.1 to 10% (W/V) aqueous solution, and the polyamine is used in an amount of 3 to 240 mg per 1 gram of dry carrier and is dissolved in a 0.1 to 20% (W/V) aqueous solution.

21 Claims, No Drawings

STABILIZATION OF CARRIER-BOUND ENZYMES BY TREATMENT WITH A BIFUNCTIONAL CROSSLINKING AGENT AND A POLYAMINE

BACKGROUND OF THE INVENTION

The present invention relates to a method for producing carrier-bound enzymes, in which a carrier which has functional groups capable of forming covalent bonds is coated with an enzyme.

When carrying out reactions catalyzed by enzymes, there is a choice of basic alternatives between homogeneously catalyzed methods using free enzymes and heterogeneously catalyzed methods using carrier-bound enzymes. Compared to free enzymes, carrier-bound enzymes have many advantages, among which their easier reusability and their outstanding suitability for processes which have to be carried out continuously deserve particular mention. Both carriers made of organic and carriers made of inorganic materials may be considered for use as carriers. Inorganic carriers have the advantage of low compressibility, particularly in an industrial-scale, continuous processes in which the carrier-bound enzymes are used in column-shaped reactors with enzyme beds of appropriate height. But whereas organic carriers often naturally have functional groups to which the enzymes can be bound, inorganic carriers as a rule do not have such functional groups. Inorganic carriers must therefore be provided with such functional groups in a separate step. Currently, treatment with silanes carrying inorganic functional groups and organic functional groups has found general acceptance as the means of choice for this purpose. The classical representative of such silanes is gamma-aminopropyl-triethoxy silane, in which an Si—O—bond to the carrier is produced through hydrolysis of the ethoxy groups, while the aminopropyl group remains as an organic functional group for forming bonds to the enzyme.

For example, U.S. Pat. No. 3,519,538, as the basic literature reference for a method of the aforementioned type, proposes to treat inorganic carriers with silanes of the type mentioned above and then to bond the enzymes to the thus functionalized carrier, referred to therein as an aminoalkyl silane derivative, either directly or by inserting a "spacer". Non-siliceous metal oxides such as aluminum oxide, hydroxyapatite or nickel oxide, and siliceous substances such as porous glass, silica, wollastonite, silica gel or bentonite are listed therein as suitable inorganic carriers.

While U.S. Pat. No. 3,519,538, having disclosed the aforementioned process, is credited with showing that inorganic carriers can be used to produce carrier-bound enzymes and how they can be so used, U.S. Pat. No. 4,230,803 develops the aforedescribed method further, in that this document teaches how the particular carrier which is optimum with regard to its pore size and pore distribution, can be determined from among several carriers under consideration, and how the concentration of the enzyme solution, with which the functionalized carrier is to be reacted, can be determined in order to obtain a maximally active preparation using a minimum amount of enzyme, the preparation also being distinguished in particular by the fact that the activity of the carrier-bound enzyme is the same or only slightly less than the activity of the enzyme in the free state.

Although excellent carrier-bound enzymes with high initial activity can be produced according to the method of U.S. Pat. No. 4,230,803, these and essentially all other carrier-bound enzymes suffer, in principle, from only limited stability, i.e. the activity of the carrier-bound enzyme decreases at a greater or lesser rate under the conditions of practical use.

U.S. Pat. No. 4,533,633 counters this drawback with a carrier-bound enzyme produced based on $SiO_2$ carriers, by contacting the substrate with shaped bodies of $SiO_2$ or alumosilicate before the reaction at the carrier-bound enzyme. Alternatively, with a type of carrier-bound enzyme which is similar as far as the carrier is concerned, U.S. Pat. No. 4,665,025 proposes to add water-soluble silicate to the substrate. However, these two last-mentioned improvements are restricted to carrier-bound enzymes with carriers which consist entirely or at least substantially of siliceous material.

The use of glutaric dialdehyde and polyethylene imine in producing carrier-bound enzymes is already known. For example, U.S. Pat. No. 4,141,857 describes the treatment of porous inorganic carriers with polyethylene imine and glutaric dialdehyde in order to produce, as stated therein, combined organic/inorganic base material from an inorganic porous carrier with an organic polymer material adsorbed and entrapped in its pores. The enzyme is then bound to the organic polymer material in a subsequent step.

The treatment of the carrier with polyethylene imine and glutaric dialdehyde thus corresponds to the previously described silanizing in that a virtual intermediate layer is produced between the carrier and the enzyme, which layer is capable on the one hand of forming a bond to the carrier—by siloxane formation in the case of silylation and by positive attachment of the polymer produced in the pores of the carrier in the case of treatment with polyethylene imine and glutaric dialdehyde——and on the other hand forming a bond to the enzyme. In other words, the "combined organic-inorganic basic material" obtained through treating porous inorganic carriers with polyethylene imine and glutaric dialdehyde corresponds to the "carriers which have functional groups capable of forming covalent bonds" defined in the general process described in the background section above.

What has been said about U.S. Pat. No. 4,141,857 also applies to U.S. Pat. No. 4,438,196 in which activated carbon is treated with polyethylene imine and glutaric dialdehyde in order to produce a product which corresponds to the combined organic/inorganic base material of U.S. Pat. No. 4,141,857.

Even more remote are processes using polyethylene imine, represented for example by European Patent No. 133,531, in which polyethylene imine, optionally in combination with other substances, is used to flocculate enzymes dissolved in water or microorganism cells suspended in water and containing intracellular enzymes. The flocculated material is then processed in further steps to form immobilized biocatalysts.

SUMMARY OF THE INVENTION

The object of the invention is therefore to provide a method which improves the stability of carrier-bound enzymes and which can also be used with those carrier-bound enzymes with carriers which consist of material other than siliceous material.

These and other objects of the invention are achieved by providing a method for producing carrier-bound enzymes in which a carrier which has functional groups capable of forming covalent bonds is coated with an enzyme, said method comprising further treating the carrier-bound enzyme in any sequence with a bifunctional cross-linking agent and a polyamine.

Whereas in U.S. Pat. No. 4,141,857 the treatment of the carrier with polyethylene imine and glutaric dialdehyde takes place before reaction with the enzyme, in contrast thereto, in the invention the treatment with polyethylene imine and glutaric dialdehyde only takes place as an additional measure when the enzyme is already bound to the carrier.

DETAILED DESCRIPTION OF PREFERRED EMBODIMENTS

According to the invention improved enzyme stability is achieved by treating the carrier-bound enzyme additionally in any sequence with a bifunctional cross-linking agent and a polyamine.

As used herein, the term "bifunctional cross-linking agent" is understood to refer to substances with two active groups, such as glutaric dialdehyde, toluene diisocyanate, hexamethylene diisocyanate, etc. Glutaric dialdehyde is especially preferred in the invention. The term "polyamine" is understood to refer to water-soluble substances containing more than one amino group such as, for example, ethylene diamine, diethylene triamine, triethylene tetramine, tetraethylene pentamine, pentaethylene hexamine, hexamethylene diamine, polyethylene imine, etc. Polyethylene imine is preferred in the invention, also polyethylene imine with a branched chain, with a molecular weight of up to 2,000,000 Daltons, preferably with a molecular weight of between 600 and 1,000,000 Daltons.

With the additional treatment according to the invention with the bifunctional cross-linking agent and the polyamine, especially with glutaric dialdehyde and polyethylene imine, it is possible to produce carrier-bound enzymes which are considerably more stable than those produced with previously known processes.

The treatment according to the invention with glutaric dialdehyde and polyethylene imine may be carried out in any sequence desired.

When treating with glutaric dialdehyde, 5 to 500 mg, preferably 25 to 250 mg, of glutaric dialdehyde are used per gram of dry catalyst material. As used herein, the term "dry catalyst material" is understood to mean the weight of the carrier treated with silane, including the enzyme bound to the carrier. Since the weights of the silane and the enzyme constitute only fractions of the weight of the carrier to which they are bound, as a first approximation the weight of the dry catalyst material can be equated with the weight of the carrier. Advantageously, the treatment is carried out with an aqueous solution of glutaric dialdehyde having a concentration (w/v) of 0.1 to 10%, preferably 0.5 to 5%, at a pH of 4 to 9, preferably 5 to 8, within a period of 15 to 120 minutes, preferably 30 to 60 minutes.

The treatment with polyethylene imine advantageously takes place with an aqueous solution of polyethylene imine having a concentration (w/v) of 0.1 to 20%, preferably 0.5 to 8%. In this case it is desirable to use 3 to 600 mg, preferably 15 to 240 mg, of polyethylene imine per gram of dry catalyst material. Advantageously a pH of 4 to 9, preferably 5 to 8, is set for the treatment. The duration of the treatment extends usefully over at least 5 minutes, preferably over at least 15 minutes. The upper time limit of treatment with polyethylene imine depends on the amount of polyethylene imine used per gram of dry catalyst material and the concentration of the polyethylene imine solution used. Experience shows that a period of up to 24 hours is sufficient, a satisfactory result being obtained after as little as 12 hours. A treatment longer than 24 hours does not produce any particularly greater effect.

In principle, any carriers which are otherwise conventional can be used as carriers in the method of the invention. Porous inorganic carriers based on metal oxide or silicate are preferred. Typical representatives which may be mentioned include aluminum oxide, zirconia, magnesium oxide, silicon dioxide, mixed oxides made of these oxides, alumosilicates and zeolites. In particular, carriers of aluminum oxide and silicon dioxide are preferred.

The enzyme to be bound may be an oxidoreductase, transferase, hydrogenase, lyase, ligase or isomerase. For the method according to the invention, those enzymes in particular are considered which are used in industrial processes, such as glucoamylase, glucose oxidase, lactase, trypsin, pepsin, papain, other proteases, lipase, pectinase, invertase, fumarase, aspartase, urease, amino-acid oxidase, penicillin acylase, or glucose isomerase. Glucose isomerase is especially preferred.

The following nonlimiting examples serve to explain the invention in further detail without limiting its scope.

PRODUCTION OF THE STARTING OR COMPARISON PREPARATIONS

Following the procedure of U.S. Pat. No. 4,230,803, in particular with regard to the determination of the optimum concentration of the enzyme solution, a carrier-bound glucose isomerase preparation was produced from an $SiO_2$ carrier with a grain size of 0.1 to 0.2 mm and a most frequent pore diameter of 430 Å, and the enzyme was additionally cross-linked with glutaric dialdehyde in accordance with one partial aspect of the invention.

In order to cross-link the enzyme the preparation was treated for 30 minutes with a fixing buffer (50 mM phosphate buffer, pH 6, containing 0.4 mM $MgSO_4$) containing glutaric dialdehyde, to which was added so much of a highly concentrated glutaric dialdehyde solution that it had a concentration (w/v) of 1% with respect to glutaric dialdehyde. The quantity of glutaric dialdehyde used was 40 mg/g of dry catalyst material. After the cross-linked preparation was washed with glutaric dialdehyde-free fixing buffer, the preparation was stored in a storage buffer (50 mM phosphate buffer, pH 6, containing 0.4 mM $MgSO_4$ and a total of 2000 ppm parahydroxybenzoic acid ester) until further use. This preparation is referred to hereinafter as "standard preparation 1".

Analogously, a carrier-bound glucose isomerase preparation was produced from an aluminum oxide carrier with a grain size of 0.3 to 0.6 mm and a most frequent pore diameter of 340 Å, and the enzyme was cross-linked with glutaric dialdehyde. This preparation is referred to hereinafter as "standard preparation 2". This preparation also was stored in a storage buffer of the type described above until further use.

EXAMPLE 1

As described for the "standard preparation 1" under "Production of the starting or comparison preparations", preparations were produced which were treated before cross-linking with glutaric dialdehyde with a 0.5% (w/v) aqueous solution of polyethylene imines (for sources see List 1), pH 5. For this purpose, the moist preparations were coated with 3 ml of the 0.5% polyethylene imine solution per gram of dry catalyst material. The mixture was incubated for 30 minutes at room temperature with occasional stirring. Subsequently, the supernatant solution was drawn off by suction and the residue washed with fixing buffer. Thereafter, the glutaric dialdehyde cross-linking was carried out as already described above and the preparations stored in the storage buffer.

| List 1 Polyethylene imines tested | | |
|---|---|---|
| Type | Manufacturer | Preparation No. |
| 7000 | BASF | Example 1/1 |
| 20000 | BASF | 1/2 |
| 80000 | BASF | 1/3 |
| Sedipur VP/FD | BASF | 1/4 |
| Sedipur VP/mf | BASF | 1/5 |
| Sedipur VP/ST | BASF | 1/6 |
| Sedipur VP/P | BASF | 1/7 |
| Polymin P | BASF | 1/8 |
| Epomin-SP-006 | Sumitomo | 1/9 |
| Epomin-SP-018 | Sumitomo | 1/10 |
| Epomin-SP-200 | Sumitomo | 1/11 |
| Epomin-SP-1000 | Sumitomo | 1/12 |

EXAMPLE 2

5 g of "standard preparation 1" were covered with 15 ml of a 0.5% (w/v) polyethylene imine solution (Polymin P, BASF), pH 5, and incubated for 30 minutes at room temperature with occasional stirring. After washing with fixing buffer, the preparation was stored in storage buffer.

EXAMPLE 3

Analogously to Example 2, "standard preparation 2" was modified with polyethylene imine.

EXAMPLE 4

Analogously to Example 1, a preparation was produced with 2% polyethylene imine solution (Polymin P, BASF).

EXPERIMENT 1

In order to demonstrate the increased stability of the carrier-bound enzymes produced according to the invention, the preparations produced in Example 1 were compared with "standard preparation 1".

To accomplish this, 1 ml of each preparation was poured into 10 cm long columns equipped with temperature-controlled jackets. The columns were subsequently charged with substrate solution. 45% (w/v) glucose solution served as substrate solution, which was adjusted to a pH of 7.5 and contained 120 ppm $Mg++$ and 200 ppm $SO_2$ in the form of $Na_2SO_3$ as co-factors. The substrate solution was preheated to 75° C. and passed through the column at a constant flow rate (volume rate 35 v/vh). As a measure of the activity of the preparations, the fructose in the flowing substrate resulting from the glucose under the influence of the carrier-bound glucose isomerase was determined polarimetrically at regular time intervals. The degree of isomerization resulting from this determination was plotted against time on simple logarithmic paper. The linear zone of the decrease in activity over time served as a measure of the stability, expressed in terms of the decrease in the degree of isomerization [%]/100 h.

In this, the stability is greater the smaller the decrease in activity in the time interval. The values obtained are listed in Table 1.

The values given for the standard preparations were obtained with a substrate which contained 1 ppm $Co++$ as well as the stated co-factors.

TABLE 1

| Stabilization effect of various polyethylene imines | |
|---|---|
| Preparation | Decrease in degree of isomerization [%]/100 h |
| Example 1/1 | 5.1 |
| 1/2 | 7.0 |
| 1/3 | 8.8 |
| 1/4 | 6.7 |
| 1/5 | 6.6 |
| 1/6 | 7.2 |
| 1/7 | 7.3 |
| 1/8 | 7.0 |
| 1/9 | 9.2 |
| 1/10 | 6.1 |
| 1/11 | 7.7 |
| 1/12 | 7.3 |
| Standard 1 | 10.7 |

EXPERIMENT 2

For comparison, Experiment 1 was repeated with some preparations under changed conditions (70° C., 30.5 v/vh). Table 2 gives the results.

TABLE 2

| Stabilization effect of various polyethylene imines | |
|---|---|
| Preparation | Decrease in degree of isomerization [%]/100 h |
| Example 1/8 | 3.5 |
| 1/9 | 3.9 |
| 1/12 | 2.9 |
| Example 2 | 4.3 |
| Standard 1 | 4.8 |

EXPERIMENT 3

In order to simulate conditions similar to those found in operation, Experiment 1 was repeated at 60° C., but was not run with a constant flow rate; instead the flow (volume rate) was set depending on the activity to a constant degree of isomerization of 46.5%. The half-life, measured in hours, was determined as a measurement for the stability. The values obtained are listed in Table 3. "Standard preparation 2" and the preparation of example 3 were also included in Experiment 3.

TABLE 3

| Half-lives of various preparations under conditions similar to those found in operation | |
|---|---|
| Preparation | Half-life* [h] |
| Standard 1 | 1260 |
| Example 1/8 | 2150 |
| Example 2 | 2200 |
| Standard 2 | 1900 |
| Example 3 | 2500 |

*The half-life was determined from the plot of ln activity → t, wherein $A_o$ was obtained by extrapolation.

EXPERIMENT 4

In order to demonstrate that the oarrier-bound enzymes according to the invention not only have better stability over time, but also have better temperature stability, Experiment 1 was repeated with "standard preparation 1" and the preparation of Example 4, with the proviso that the substrate solution was preheated to 70° C., 75° C. and 80° C. and corresponding thereto, the flow was adjusted to rates by volume of 30.5 v/vh, 35 v/vh and 41 v/vh, respectively. As in Experiment 1, the decrease in activity per 100 hours, expressed in % degree of isomerization, was used as a measure of the stability. The values obtained are listed in Table 4.

TABLE 4

| Temperature [°C.] | Decrease in the degree of isomerization [%]/100 h Preparation | |
|---|---|---|
| | Standard 1 | Example 4 |
| 70 | 4.8 | 2.0 |
| 75 | 10.7 | 6.8 |
| 80 | 60.3 | 42.2 |

The foregoing description and examples have been set forth merely to illustrate the invention and are not intended to be limiting. Since modifications of the described embodiments incorporating the spirit and substance of the invention may occur to persons skilled in the art, the scope of the invention is to be limited solely with reference to the appended claims and equivalents.

What is claimed is:

1. A method for producing carrier-bound enzymes having improved stability comprising the steps of:
   (a) providing a granular carrier which has functional groups capable of forming covalent bonds and which is coated with an enzyme to produce a carrier-bound enzyme, and
   (b) contacting said carrier-bound enzyme in any sequence with an amount of 5 to 250 mg per 1 gram of dry carrier-bound enzyme of a bifunctional cross-linking agent contained in a 0.1 to 10% (w/v) aqueous solution of the cross-linking agent and with an amount of 3 to 240 mg per 1 gram of dry carrier-bound enzyme of a polyamine contained in a 0.1 to 20% (w/v) aqueous solution of said polyamine,
   whereby a granular carrier-bound enzyme is produced.

2. A method according to claim 1, wherein the carrier-bound enzyme is first treated with the polyamine and then with the cross-linking agent.

3. A method according to claim 1, wherein glutaric dialdehyde is used as the bifunctional cross-linking agent.

4. A method according to claim 1, wherein treatment is carried out with 25 to 250 mg glutaric dialdehyde per gram of dry catalyst material.

5. A method according to claim 1, wherein glutaric dialdehyde in a in a 0.5 to 5% (w/v) aqueous solution is used as the bifunctional cross-linking agent.

6. A method according to claim 3, wherein the treatment with glutaric dialdehyde takes place at a pH between 4 and 9.

7. A method according to claim 6, wherein the treatment with glutaric dialdehyde takes place at a pH between 5 and 8.

8. A method according to claim 3, wherein the treatment with glutaric dialdehyde is carried out for 15 to 120 minutes.

9. A method according to claim 8, wherein the treatment with glutaric dialdehyde is carried out for 30 to 60 minutes.

10. A method according to claim 1, wherein polyethylene imine is used as the polyamine.

11. A method according to claim 10, wherein polyethylene imine with a molecular weight of up to 2,000,000 Daltons is used as the polyamine.

12. A method according to claim 11, wherein polyethylene imine with a molecular weight of from 600 to 1,000,000 Daltons is used as the polyamine.

13. A method according to claim 1, wherein treatment is carried out with 15 to 240 mg polyethylene imine per gram of dry catalyst.

14. A method according to claim 1, wherein polyethylene imine is used in a 0.5 to 8% (w/v) aqueous solution.

15. A method according to claim 10, wherein the treatment with polyethylene imine is carried out at a pH between 4 and 9.

16. A method according to claim 15, wherein the treatment with polyethylene imine is carried out at a pH between 5 and 8.

17. A method according to claim 10, wherein the treatment with polyethylene imine is carried out for at least 5 minutes.

18. A method according to claim 17, wherein the treatment with polyethylene imine is carried out for at least 15 minutes.

19. A method according to claim 1, wherein said carrier is a porous inorganic carrier selected from aluminum oxide or silicic acid.

20. A method according to claim 1, wherein glucose isomerase is used as the enzyme.

21. A method according to claim 1, wherein said enzyme is covalently bonded to said carrier.

* * * * *